United States Patent [19]

Liauw et al.

[11] Patent Number: 4,605,665
[45] Date of Patent: Aug. 12, 1986

[54] SYSTEMIC TREATMENT OF SPLANCHNIC ISCHEMIA SHOCK USING 7-CHLORO-N-(3,4-DICHLOROPHENYL)-2,3-DIHYDRO-5-HYDROXY-1-BENZOTHIEPIN-4-CARBOXAMIDE 1,1-DIOXIDE AND PHARMACEUTICALLY ACCEPTABLE SALTS THEREOF

[75] Inventors: Hui L. Liauw, Wycoff; Howard H. Oei, Basking Ridge; Edmond C. Ku, Upper Saddle River, all of N.J.

[73] Assignee: Ciba-Geigy Corporation, Ardsley, N.Y.

[21] Appl. No.: 706,588

[22] Filed: Feb. 28, 1985

[51] Int. Cl.[4] ............................................. A61K 31/38
[52] U.S. Cl. ................................................... 514/431
[58] Field of Search ........................................ 514/431

Primary Examiner—Stanley J. Friedman
Attorney, Agent, or Firm—Michael W. Glynn; Irving M. Fishman

[57] ABSTRACT

Shock induced by splanchnic ischemia can be treated or prevented by the administration of an effective cyclooxygenase and lipoxygenase inhibiting amount of a compound of the formula

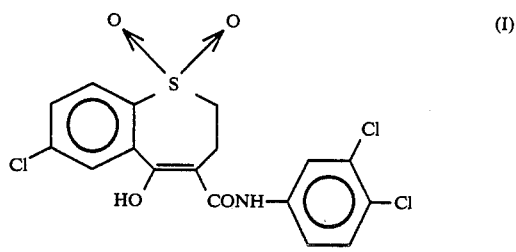

or a pharmaceutically acceptable salt thereof to a mammal in need of the same.

4 Claims, No Drawings

SYSTEMIC TREATMENT OF SPLANCHNIC ISCHEMIA SHOCK USING 7-CHLORO-N-(3,4-DICHLOROPHENYL)-2,3-DIHYDRO-5-HYDROXY-1-BENZOTHIEPIN-4-CARBOXAMIDE 1,1-DIOXIDE AND PHARMACEUTICALLY ACCEPTABLE SALTS THEREOF

Elevation of circulating eicosanoids have been recognized in various types of shock associated with splanchnic ischemia. Several of these arachidonic acid metabolites have been implicated in the production of circulatory failure in shock.

It has now been discovered that the compound of the formula

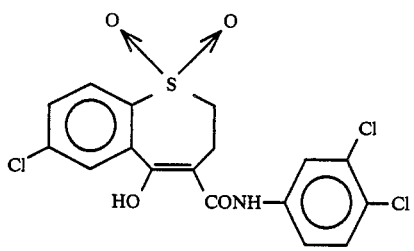

and the pharmaceutically acceptable salts thereof are highly effective in the prevention and treatment of the various types of shock associated with splanchnic ischemia by administering an effective endogenous cyclooxygenase and lipoxygenase inhibiting amount of such compounds to a mammal, including man in need of the same.

The compounds of formula I and the pharmaceutically acceptable salts thereof are known and disclosed in U.S. Pat. No. 4,185,109 issued Jan. 22, 1980. This patent discloses such compounds as useful antiinflammatory agents, for example, in the treatment of arthritic conditions, and dermato-pathologic conditions of the type associated with inflammation, inter alia, as determined by carrageenin paw-edema screening tests. Aspirin, a widely prescribed well known antiinflammatory agent, is similarly indicated for the treatment of arthritic conditions and dermato-pathologic conditions of the type associated with a positive response in standard carrogeenin paw-edema screening tests. However, aspirin may exacerbate shock induced by splanchnic ischemia.

Surprisingly and unexpectedly, the compound of formula I and its pharmaceutically acceptable salts are highly effective in the prevention and treatment of shock associated with splanchnic ischemia. For example, pretreatment with intravenous 7-chloro-N-(3,4-dichlorophenyl)-2,3-dihydro-5-hydroxy-1-benzothiepin-4-carboxamide 1,1-dioxide monosodium salt monohydrate, administered in an amount of 5 mg/kg to dogs and sufficient to suppress the biosynthesis of cyclooxygenase and lipoxygenase dependent products, has been found to be effective in moderating the hemodynamic abberrations in dogs subjected to a three hour occlusion of the splanchnic arteries (SAO), in that 90% survived with treatment versus only 12% in the absence of pretreatment.

The compound of formula I and its pharmaceutically acceptable salts are advantageously administered parenterally, preferably intravenously, in order to insure rapid assimilation of the compound in the host.

Suitable pharmaceutically acceptable salts of the compound of formula I include the sodium, potassium, ammonium, mono-, di- or trimethyl- or -ethylammonium, ethanolammonium, diethanolammonium, triethanolammonium, glucamine, pyrrolidinium, piperidinium or morpholinium salt thereof. One expecially preferred salt is the sodium salt monohydrate of the compound of formula I, also known as enolicam sodium.

The amount of compound of formula I or pharmaceutically acceptable salt thereof administered is advantageously between about 1 to about 50 mg/kg, preferably between about 2 to about 25 mg/kg based upon the weight of the host mammal.

The compound of formula I and is pharmaceutically acceptable salts are advantageously administered in the form of stable solutions or suspensions in the presence of one or more pharmaceutically acceptable excipients. Suitable liquid excipients include water, ethanol and mixtures thereof, advantageously buffered with pharmaceutically acceptable pH adjusting agents. For veterinary purposes, dimethylacetamide may be used as an acceptable carrier.

What is claimed is:

1. A method of treating shock induced by splanchnic ischemia in a mammal by parenterally administering an effective cyclooxygenase and lipoxygenase inhibiting amount of a compound of the formula

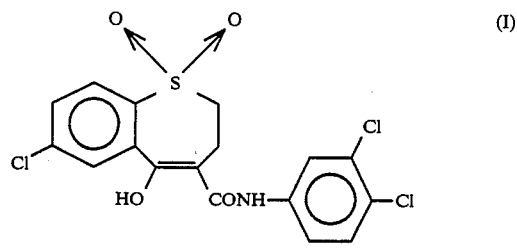

or a pharmaceutcally acceptable salt thereof to said mammal in need of the same.

2. A method according to claim 1 wherein the administration is intravenous.

3. A method according to claim 1, wherein the compound is in the form of its sodium salt.

4. A method according to claim 2, wherein the compound is in the form of sodium salt.

* * * * *

UNITED STATES PATENT AND TRADEMARK OFFICE
CERTIFICATE OF CORRECTION

PATENT NO. : 4,605,665

DATED : August 12, 1986

INVENTOR(S) : Hui L. Liauw, Goward H. Oei, Edmond C. Ku

It is certified that error appears in the above-identified patent and that said Letters Patent is hereby corrected as shown below:

Column 2, Claim 4, Line 2, after "of" insert --its--.

Signed and Sealed this

Twenty-eighth Day of April, 1987

*Attest:*

DONALD J. QUIGG

*Attesting Officer*　　　*Commissioner of Patents and Trademarks*